United States Patent [19]

Chung et al.

[11] Patent Number: 5,206,373
[45] Date of Patent: Apr. 27, 1993

[54] PROCESS FOR PREPARING FIBRINOGEN RECEPTOR ANTAGONISTS

[75] Inventors: John Y. L. Chung, Edison; David L. Hughes, Old Bridge; Dalian Zhao, Scotch Plains, all of N.J.

[73] Assignee: Merck & Co., Inc., Rahway, N.J.

[21] Appl. No.: 843,658

[22] Filed: Feb. 28, 1992

[51] Int. Cl.$^5$ ............................................. C07D 213/00
[52] U.S. Cl. ................................... 546/335; 546/235
[58] Field of Search ................... 546/335, 235

[56] References Cited

U.S. PATENT DOCUMENTS 4,004,008  1/1977  Makovec et al. ............... 424/248.54

FOREIGN PATENT DOCUMENTS 381033  8/1990  European Pat. Off. .
384362  8/1990  European Pat. Off. .

OTHER PUBLICATIONS

Singerman et al, *Journal of Heterocyclic Chemistry*, vol. 3, No. 1, pp. 74–78, Mar. 1966.

Solar et al, *Journal of Organic Chemistry* vol. 31 pp. 1996–1997, 1966.

Merck Index 10th ed., paragraph 9301.

*Primary Examiner*—C. Warren Ivy
*Assistant Examiner*—Zinna N. Davis
*Attorney, Agent, or Firm*—Charles M. Caruso; Richard S. Parr

[57] ABSTRACT

The invention is a highly efficient synthesis for making compounds of the formula:

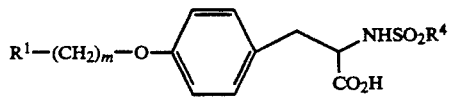

wherein:
$R^1$ is a six member saturated or unsaturated heterocyclic ring containing one or two heterocyclic atoms wherein the heteroatoms are N; or $NR^6$, wherein $R^6$ is H or $C_{1-10}$ alkyl;
m is an integer from two to six; and
$R^4$ is aryl, $C_{1-10}$ alkyl, or $C_{4-10}$ aralkyl.

4 Claims, No Drawings

PROCESS FOR PREPARING FIBRINOGEN RECEPTOR ANTAGONISTS

BACKGROUND OF THE INVENTION

European Publication No. 478,363, published Apr. 1, 1992, describes fibrinogen receptor antagonists and procedures for preparing fibrinogen receptor antagonists which are prepared according to the procedure of the present invention. In particular, the compound:

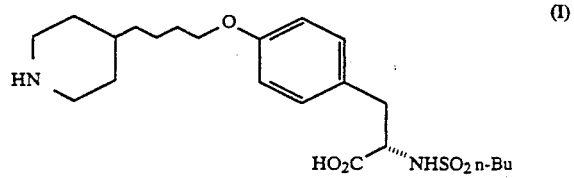

is prepared according to an 11-step procedure involving the formation of potentially hazardous NaH/DMF for ether formation, which required a chromatographic purification.

Singerman et al., *J. Heterocyclo Chem.* (1966), 3, 74, describes a procedure for preparing 4-(4-pyridinyl)-butyl chloride, which requires 6 steps. The procedure of the invention requires only one step to prepare this compound.

Solar et al., *J. Org. Chem.* (1966), 31, 1996, describes O-alkylation of tyrosine. Selective O-alkylation of N-sulfonylated tyrosine described in the present invention is unprecedented.

SUMMARY OF THE INVENTION

The invention is a highly efficient synthesis for making compounds of the formula:

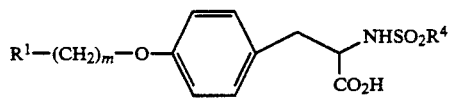

wherein:
$R^1$ is a six member saturated or unsaturated heterocyclic ring containing one or two heteroatoms wherein the heteroatoms are N; or $NR^6$, wherein $R^6$ is H or $C_{1-10}$ alkyl;
m is an integer from two to six; and
$R^4$ is aryl, $C_{1-10}$ alkyl, or $C_{4-10}$ aralkyl.

DETAILED DESCRIPTION OF THE INVENTION

The invention is a process for preparing fibrinogen receptor antagonists of the formula:

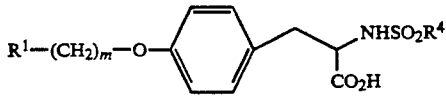

(II)

wherein:
$R^1$ is a six member saturated or unsaturated heterocyclic ring containing one or two heteroatoms wherein the hetero atoms are N; or $NR^6$ wherein $R^6$ is H or $C_{1-10}$ alkyl;
m is an integer from two to six; and
$R^4$ is aryl, $C_{1-10}$ alkyl, or $C_{4-10}$ aralkyl,
according to the procedure whereby

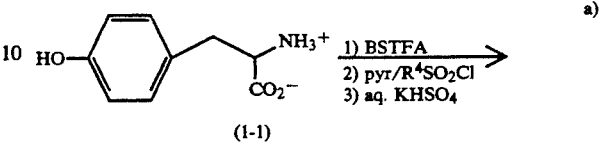

a)

tyrosine or tyrosine-derivative (1-1) is subjected to bis-trimethylsilyl trifluoracetamide (BSTFA) mediated sulfonylation, using $R^4SO_2Cl$, in acetonitrile, to give the corresponding sulfonamide (1-2);

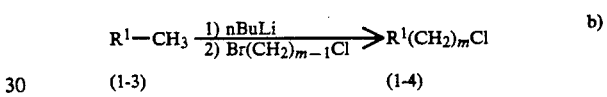

b)

methylated $R^1$ (1-3) is reacted with nBuLi, before quenching with a straight chain alkyl group having Br at one end and Cl at the other end, to yield $R^1(CH_2)_mCl$ (1-4);

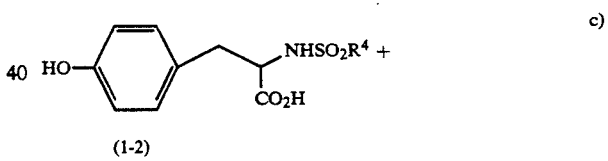

c)

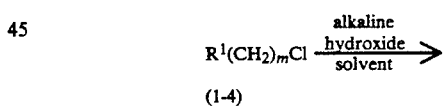

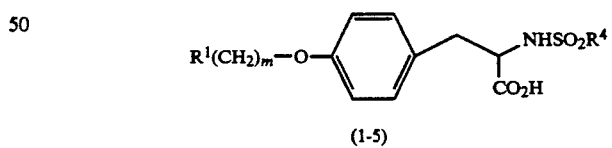

(1-2) is added to (1-4) and subjected to phenolic O-alkylation in alkaline hydroxide, preferably 3N KOH, in polar aprotic solvents, such as 1,3-dimethyl-3,4,5,6-tetrahydro-2(1H)-pyrimidinone (DMPU), methyl sulfoxide (DMSO), N-methylpyrrolidinone (N-MP), 1,3-dimethyl-2-imidazolidinone (DMEU), tetramethylurea (TMU), or N,N-dimethylacetamide (DMA), preferably highly aprotic solvents such as DMPU or DMSO, more preferably DMSO, preferably at about 65° C.

When $R^1$ is pyridine, selective hydrogenation is achieved using Pd/C in acetic acid.

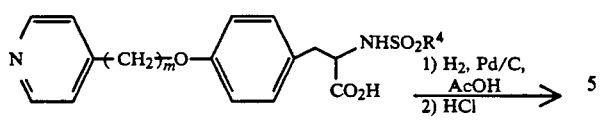

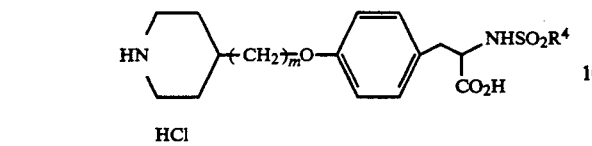

Preferably, the invention is a highly efficient synthesis for making:

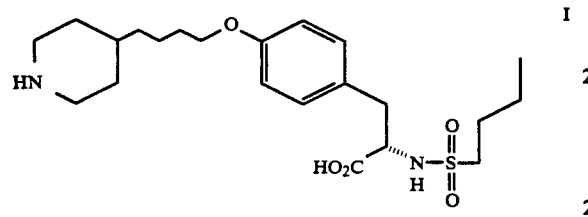

The synthesis uses trimethylsilyl groups as temporary protection, enabling selective sulfonylation to be carried out in a one-pot synthesis using L-tyrosine itself.

The synthesis preferably employs 1) use of 4-picoline as latent form of piperidine, which eliminates the need for a protecting group, and 3-carbon homologation with 3-bromo-1-chloropropane via the 4-picolyllithium;

2) temporary bis-O,O'-silylation of (L)-tyrosine by BSTFA which provides selective N-sulfonylation with n-BuSO$_2$Cl to give the sulfonamide in high yield and free of racemization in one step;

3) selective high yielding phenyl ether formation using the simple reagent aqueous alkaline base (NaOH or KOH; preferably 3N KOH) in DMPU (1,3-dimethyl-3,4,5,6-tetrahydro-2(1H)-pyrimidinone) or DMSO; and 4) selective hydrogenation of the pyridine ring in the presence of the tyrosine ring using Pd/C in acetic acid.

The synthesis of the invention uses inexpensive starting materials and reagents, and avoids prior art processing steps using potentially hazardous NaH/DMF mixtures to induce ether formation, which required a chromatographic purification. The present invention synthesis requires no such chromatographic purification.

EXAMPLE 1

According to the procedure of the present invention, the following compound:

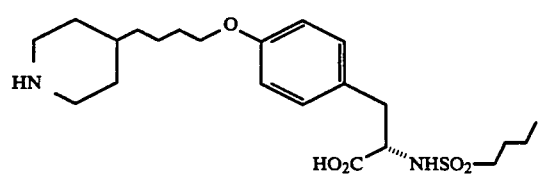

was prepared. The four process steps are outlined below:

Step 1

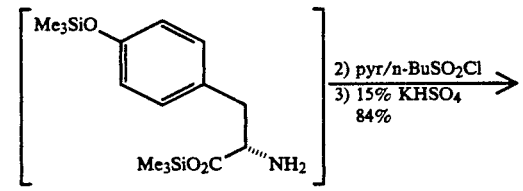

Step 2

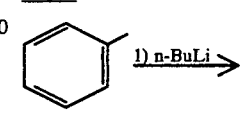

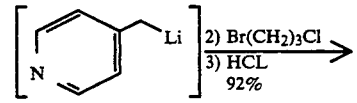

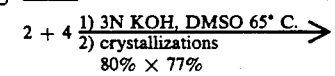

Step 3

2 + 4 $\xrightarrow[\text{2) crystallizations}]{\text{1) 3N KOH, DMSO 65° C.}}$
             80% × 77%

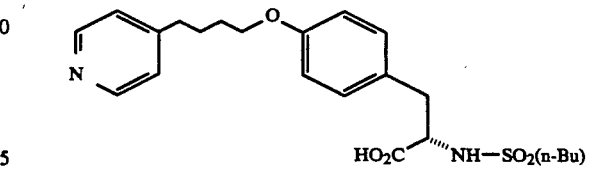

Step 4

5 $\xrightarrow[\text{2) aq. HCl}]{\text{1) H}_2\text{Pd/C, AcOH}}$
         94%

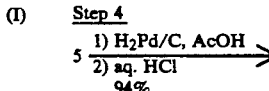
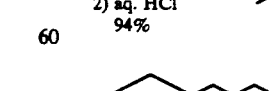

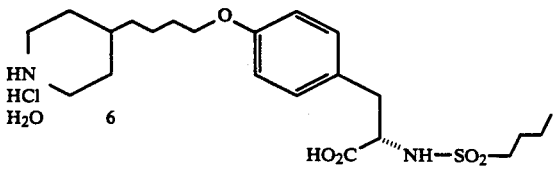

Step 1: N-n-BuSO₂-(L)-tyrosine (2)

A 50 L four-neck round bottom flask equipped with a mechanical stirrer, condenser, nitrogen inlet, HCl trap, heating unit and a thermometer probe was purged with nitrogen overnight and then charged with L-tyrosine (1040 g, 5.74 mol) 1, CH₃CN (20.8 L), N,O-bis-trimethylsilyl-trifluoromethyl-acetamide (3103 g, 12.054 mol). The suspension was heated at 85° C. to gentle reflux for 2 h. The resulting clear solution, which by ¹H NMR was mainly O,O'-bis-trimethylsilyl-(L)-tyrosine, was cooled to 40° C., and pyridine (544.84 g, 6.888 mol) and n-BuSO₂Cl (989.0 g, 6314 mol) were slowly added over 30 minutes. The reaction mixture was then aged at 70° C. for 3 hours and at room temperature for 14 hours. Almost all the solvent was removed in a batch concentrator, and the resulting oily residue was treated with 15% KHSO₄ (20.8 L) and stirred vigorously for 1 hour. The mixture was extracted with i-propyl acetate (3×6.2 L). The combined organic layer was treated with Ecosorb ™ S-402 (3.12 kg) and stirred at room temperature overnight. Ecosorb ™ was removed by filtration and the filter cake was washed with i-propyl acetate (4.2 L). The filtrate was evaporated to dryness and the resulting yellow oil was dissolved in hot EtOAc (45°–50° C., 1.25 L). Hexane (3.74 L) was added slowly to the stirring solution and the resulting slurry was stirred at room temperature overnight. The solid was collected by filtration and the filter cake was washed with EtOAc/hexane (0.2 L/1.89 L). After drying under vacuum, 1457 g (84%) of 2 was obtained as a white solid.

HPLC Assay: 99.6A %; RT=7.55 min; Zorbax RX-C8 column, 4.6 mm×25 cm ID; 220 nm; 1.5 mL/min; linear gradient 10 to 90% A over 10 min, A=CH₃CN, B=0.1% aqueous $H_3PO_4$. mp 125°–126.5° C.; $[\alpha]^{25}D = -25.2°$ (c 0.80, MeOH); MS(EI) m/z 301 (M+).

¹H NMR (CD₃OD) δ0.81 (t, J=7.2 Hz, 3H), 1.24 (m, 2H), 1.45 (m, 2H), 2.61 (t, J=7.9 Hz, 2H), 2.73 (A of ABX, $J_{AB}$=13.8 Hz, $J_{AX}$=9.8 Hz, 1H), 3.07 (B of ABX, $J_{BA}$=13.8 Hz, $J_{BX}$=4.7 Hz, 1H), 4.07 (X of ABX, $J_{XA}$=9.8 Hz, $J_{XB}$=4.7 Hz, 1H), 6.72 (d, J=8.4 Hz, 2H), 7.10 (d, J=8.4 Hz, 2H).

¹³C NMR (CD₃OD) δ13.9, 22.5, 26.5, 39.1, 54.1, 59.5, 116.3, 129.2, 131.6, 157.5, 175.3.

Anal. Calcd for $C_{13}H_{19}O_5SN$: C, 51.81; H, 6.35; N, 4.65; S, 10.64. Found: C, 51.73; H, 6.28; N, 4.60; S, 10.82.

Step 2: 4-(4-Pyridinyl)butyl chloride HCl salt (4)

In the preparation of 4-(4-pyridinyl)butyl chloride, heating 4-picoline and n-BuLi at 40° C. for 2 hrs was necessary to effect complete consumption of n-BuLi. If not heated, some unreacted n-BuLi will trans-metallate with 3-bromo-1-chloropropane to give n-butyl bromide which then reacts with 4-picolyllithium to give 4-pentylpyridine. Reversed addition of 4-picolyllithium to 3-bromo-1-chloropropane at ≦−65° C. was critical for avoiding the formation of bis-alkylation product, 1,5-bis-(4-pyridinyl)-pentane. Complete elimination of THF and water were important for the smooth formation of the HCl salt, since THF reacts with HCl to give 4-chlorobutanol, which increases the solubility of the HCl salt and lowers its recovery, and the presence of water makes filtration of the HCl salt very difficult due to the gummy nature of the hydrate. When these precautions were taken, 4-(4-pyridinyl)butyl chloride hydrochloride salt (4) was prepared in 92% yield and 98% purity.

A 22 L four-neck round bottom flask equipped with a mechanical stirrer, condenser, addition funnel with side-arm and a thermometer probe was purged with nitrogen overnight. THF (4.1 L) and 4-picoline (838.2 g, 9.0 mol) were added and the batch was cooled to ≦−70° C. n-Butyllithium (7.02 L of 1.41M) in hexane was added slowly while keeping the internal temperature ≦−50° C.

The addition took about 1 h to give an orange solution with some precipitate. When the reaction was carried out at 0° C., significant decrease in yield and increase in formation of impurities were observed.

The dry ice bath was removed and the batch was allowed to warm to room temperature and then heated at 40°–45° C. for 2 h.

Heating at 40°–45° C. was the optimal temperature to effect complete lithiation of 4-picoline without decomposition. Without this heating, unreacted n-BuLi transmetalated with 3-bromo-1-chloropropane to give 1-n-butyl bromide. It then reacted with 4-picolyllithium to give 4-pentylpyridine which could not be separated from the desired product. Heating at higher temperature led to significant decomposition.

THF (4.1 L) was added to dissolve the 4-picolyllithium slurry to give a deep orange solution. The batch was cooled to 0° C., then added carefully via a polypropylene tube using a pneumatic pump to a −75° C. solution of 3-bromo-1-chloropropane in THF (1.5 L) in a dry 50 L three-neck round bottom flask equipped with a mechanical stirrer, nitrogen inlet/outlet and a thermometer probe, while keeping the internal temperature ≦−65° C.

The reaction of 4-picolyllithium and 3-bromo-1-chloropropane was exothermic. It was extremely critical to keep internal temperature less than −65° C. to avoid the reaction of the desired product with 4-picolyllithium to give 1,5-bis-(4-pyridinyl)-pentane. The addition took about 2 h.

The batch was allowed to gradually warm to 0° C. overnight and then worked up by adding 9 L water, stirring for 10 min, separating layers and extracting aqueous layer with i-propyl acetate (5 L). The combined organic layers were concentrated in vacuo at 40° C. to one-third of the original volume in a batch concentrator fitted with 2 additional traps between the receiver and the house vac line, then i-propyl acetate (6 L) was added and again concentrated to one-third of the original volume.

Complete removal of THF and water by i-propyl acetate azeotrope was critical for smooth formation of HCl salt. THF reacts with HCl to give 4-chlorobutanol which increases the solubility of the HCl salt and lowers its recovery. The presence of water gives a gummy solid which makes filtration of the HCl salt very difficult.

The batch was cooled to −10° C. and then treated with a solution of 9.0 mol of HCl in 3 L i-propyl acetate.

HCl in i-propyl acetate was prepared the day before by bubbling HCl gas into i-propyl acetate at −10° C. until 9.1 mole of HCl was accumulated (by weight) and stored at room temperature. The loss of HCl was about 1%. Addition of HCl to the batch was exothermic. Temperature rose to +35° C.

After stirring for 1 h, the resulting slurry was transferred via a polypropylene tube using pneumatic pump into a nitrogen-filled enclosed coarse filter funnel placed under vacuum. The solid was washed several times with THF (4.5 L total volumn) and dried with a stream of nitrogen under reduced pressure to give 1710.4 g (92%) of 4 as a white solid.

HPLC Assay: 92% area; RT=2.40 min; Zorbax RX column, 4.6 mm×25 cm ID; 220 nm; 1.5 mL/min; isocratic 50%/50% A/B, A=CH₃CN, B=0.01M decanesulfonic acid sodium salt in 0.1% aqueous $H_3PO_4$. 4-Picoline at RT=1.7 min.

mp 119°-120.5° C.; MS(CI) m/z 169 (M+—HCl).

¹H NMR (CD₃OD) δ1.79-2.00 (m, 4H), 3.01 (t, J=7.3 Hz, 2H), 3.36 (t, J=6.1 Hz, 2H), 8.00 (d, J=6.7 Hz, 2H), 8.75 (d, J=6.7 Hz, 2H);

¹³C NMR (CD₃OD) δ28.1, 33.0, 36.1, 45.3, 128.6, 142.2, 166.1;

Anal. Calcd for $C_9H_{13}NCl_2$: C, 52.45; H, 6.36; N, 6.80; Cl, 34.40. Found: C, 52.22; H, 6.40; N, 6.51; Cl, 34.11.

Step 3: Phenyl Ether 5 Formation

In the KOH-mediated coupling reaction, urea-based solvents (DMPU, DMEU, TMU) and DMSO gave the best assay yields, 85-96%. DMA and N-MP gave assay yields in the low 80's. DMPU was found to be the optimal solvent in minimizing the formation of the bis-alkylated product (1%), where as DMSO gave the highest amount of bis-alkylated product (2%).

Ether Formation and Purification

Step 3a

To a 50 L four-neck round bottom flask equipped with a mechanical stirrer, condenser, nitrogen inlet and a thermometer probe was charged N-n-butanesulfonyl-(L)-tyrosine (1386.3 g, 4.60 mol), 4-(4-pyridinyl)-butyl chloride.HCl (1137.8 g, 5.52 mol) and DMSO (16.56 L). With vigorous stirring, 3N aq. KOH (5.52 L, 16.56 mol) was added over 15 min.

The mixing of the 3N aq. KOH with the rest of the material was somewhat exothermic. The temperature was maintained in the 30°-40° C. range for this operation using cooling water.

Potassium iodide (7.64 g, 46.0 mmol) was added, and the mixture was heated at 65° C. for 24 h and 60° C. for 12 h (or until 95% completion as judged by HPLC analysis). After cooling to room temperature, the mixture was diluted with 0.25N NaOH (46 L) and extracted once with t-butyl methyl ether (23 L). The aqueous layer was treated with Ecosorb S-402 (2.0 kg) and Nuchar SA (150 g) and the resulting mixture (~67 L) was mechanically stirred for 1 h. The mixture was filtered through a coarse-porosity sintered funnel and the filtered cake was washed with 69 L DI water. The combined filtrate (~136 L) was placed in a 200 L vessel

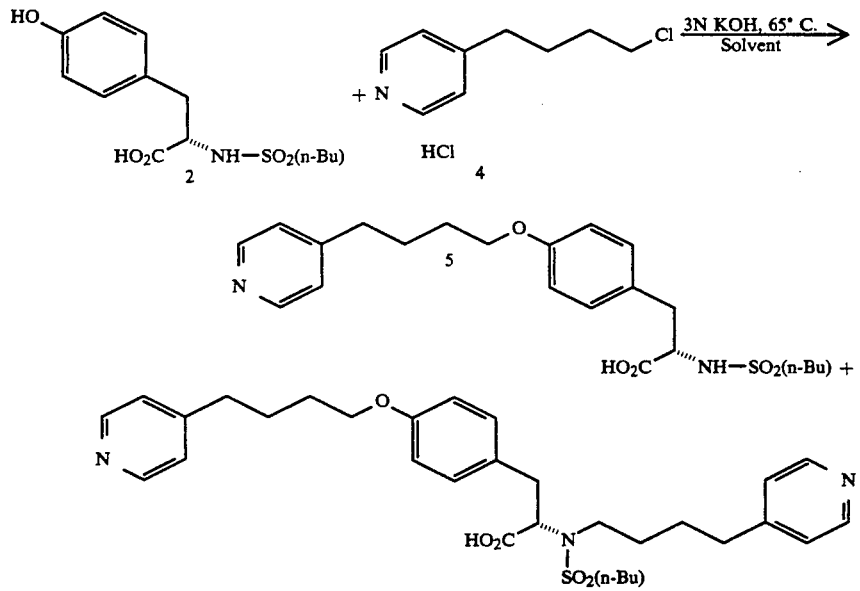

A direct isolation method for the coupled product was developed, which avoided the large usage of methylene choride for extraction. Ecosorb treatment of the aqueous-diluted reaction mixture, and filtration followed by pH adjustment to its isoelectric point (pH 4.8) provided an 80% yield of the crude product in 93-95 A % purity. Subsequent pH adjustment (pH 5.5) and two swishings in 10% AcOH/water removed the unreacted n-BuSO₂-Tyr and bis-impurity to give 99+ A % pure beige solid in 77% isolated yield. If bis-impurity is still present at an unacceptable amount (>0.1 A %), another swishing in 10% AcOH/water should be carried out. Alternatively, the pH can be adjusted to 5.5 rather than pH 4.8 at the point after Ecosorb treatment and filtration so that it combines the precipitation of the product and the elimination of n-BuSO₂-Tyr in one step. This will eliminate one isolation.

equipped with a pH meter probe and a mechanical stirrer. With vigorous stirring, NaCl (2.5 kg) was added, stirred for 30 min, and then 50% aq. acetic acid (~4 L) was added until pH 4.80, and stirring continued for 2-3 h.

Initial pH was about 13.3. When pH was near 4.8, some brown gummy material along with beige solid were formed. Prolonged stirring was needed to complete the turnover to crystalline material. If pH is below 4.8, dilute NaOH should be added.

The resulting slurry was filtered through a coarse-porosity sintered funnel, and the cake was washed with 23 L DI water. The crude product was dried at 40° C. under house-vacuum under a positive nitrogen pressure for 20 h to give 1599 g (80%) of a mixture of brown and beige solid having a wt % purity of 95%.

Major impurities are the tyrosine starting material (0.75 A %) and the bis-alkylated product (2.75 A %). The mother liquors and wash combined contained about 10% of the product by LC assay. HPLC Assay: product 5, 96% area; RT=6.76 min; tyrosine 1, RT=7.66 min; bis-alkylated product, RT=6.20 min; Zorbax RX-C8 column, 4.6 mm×25 cm ID; 220 nm; 1.5 mL/min; linear gradient 10 to 90% A over 10 min, A=CH$_3$CN, B=0.1% aqueous H$_3$PO$_4$.

Step 3b

The solid was further purified to 99.4 A % purity by the following procedures.

It is critical to remove both impurities at this stage before subjecting the material to the hydrogenation, since the hydrogenated bis-impurity and tyrosine 1 are extremely difficult to remove.

To a 50 L RB flask equipped with a thermometer probe and addition funnel was charged the crude 5 (1.50 kg, 3.45 mol) and 0.25N NaOH (19.33 L, 4.83 mol). After complete dissolution of the solid by gentle heating at 60°-70° C. for a few minute, 0.25N NaHCO$_3$ (4.83 L, 1.21 mol) was added. The solution was cooled to room temperature, and adjusted to pH 7 by slow additon of 1N HCl (~2.65 L). The solution was further brought down to pH 5.5 by slow addition of 0.5N HCl (~5.10 L). Stirring was continued for 1 h, then the slurry was filtered through a coarse funnel padded with a sheet of shark-skin paper and a polypropylene pad (10 μm) and the cake was washed with DI H$_2$O (10 L). The solid was dried under house vacuum with nitrogen sweep to give 1.42 kg of beige solid.

This treatment removed most of the tyrosine 1. The sample at this stage should contain ≦0.1 area % of 1. Subsequent swishings in 10% AcOH/H$_2$O removed the bis-alkylated impurity. Filtration of the solid slurry using a M-porosity sintered glass funnel is not recommended due to extremely low flow rate. C-porosity sintered glass funnel should not be used due to some breakthrough.

The solid was suspended in 10% acetic acid in water (1 g/15 mL), and heated with steam to 80° C. for 5 min, then allowed to cool slowly to room temperature overnight. After stirring for 18 h, the solid was collected on a coarse funnel padded with a sheet of shark-skin paper and a polypropylene pad (10 μm), washed with DI water (20 L) and partially dried using house vacuum with nitrogen sweep for several hours. This swishing was repeated and the solid was washed with DI water (20 L), methanol (3×4 L) and vacuum dried at 35° C. with nitrogen sweep for two days. 1.16 kg (77%; 62% overall) of off-white solid was obtained.

Subsequent study showed that methanol washings were not necessary. About 5% of the material was lost in this operation. If the level of bis-alkylated impurity is greater than 0.1%, another acetic acid/water swishing should be carried out.

HPLC Assay: product 5, 99.8% area; RT=6.76 min; tyrosine 1, RT=7.66 min; bis-alkylated product, RT=6.20 min; Zorbax RX-C8 column, 4.6 mm×25 cm ID; 220 nm; 1.5 mL/min; linear gradient 10 to 90% A over 10 min, A=CH$_3$CN, B=0.1% aqueous H$_3$PO$_4$.

mp 137°-138° C.; [α]$^{25}$D= −14.7° (c 0.91, MeOH); MS(CI) m/z 435 (MH+).

$^1$H NMR (CD$_3$OD) δ0.86 (t, J=7.3 Hz, 3H), 1.33 (hex, J=7.3 Hz, 2H), 1.68 (m, 2H), 1.83 (m, 2H), 2.82 (m, 2H), 3.06 (A of ABX, J$_{AB}$=13.9 Hz, J$_{AX}$=6.3 Hz, 1H), 3.16 (B of ABX, J$_{BA}$=13.9 Hz, J$_{BX}$=5.0 Hz, 1H), 3.90 (t, J=5.7 Hz, 2H), 4.32 (X of ABX, J$_{XA}$= 6.3 Hz, J$_{XB}$=5.0 Hz, 1H), 6.72 (d, J=8.6 Hz, 2H), 7.17 (d, J=8.6 Hz, 2H), 7.33 (d, J=6.3 Hz, 2H), 8.49 (d, J=6.3 Hz, 2H).

$^{13}$C NMR (CDCl$_3$) δ13.5, 21.5, 25.4, 26.5, 28.6, 35.1, 38.9, 53.0, 57.9, 67.0, 114.3, 125.0, 128.7, 130.8, 145.9, 155.8, 157.7, 175.0.

Anal. Calcd for C$_{22}$H$_{30}$O$_5$SN$_2$: C, 60.81; H, 6.96; N, 6.45; S, 7.38. Found: C, 60.53; H, 6.88; N, 6.26; S, 7.65.

Step 4: Hydrogenation

Finally, selective hydrogenation of the pyridine ring to piperidine ring was accomplished by using 5 wt % of 10% Pd/C in AcOH at 60° C. to give the target product cleanly without reduction of the phenolic ring. Hydrogenation is monitored carefully by HPLC and $^1$HNMR when theoretical uptake of hydrogen is near. As soon as consumption of the starting material is complete, the hydrogenation should be terminated. Filtration of the reaction mixture, evaporation of acetic acid followed by crystallizing the product from 6% AcOH/water gave 6 free base. Trace amounts of starting material were removed by swishing in 6% AcOH/water. Treatment of the free base with 2.5 volume % concentrated HCl (2.1 eq.) in i-propyl acetate provided the 5 (hydrochloride) monohydrate in 94% overall yield as a white to off-white solid in ≧99.7 A % purity with two impurities both at 0.1 A % level.

Step 4a

Phenyl ether 5 (1.051 kg, 2.42 mol) and 10% Pd/C (53 g, 5 wt %) in acetic acid (14 L) was hydrogenated in a 5-gallon stainless steel vessel at 40 psi and 60° C. The reaction was sampled hourly when near completion and terminated as soon as complete consumption of starting material was observed (took 5.5 h). Longer reaction time led to formation of impurities.

1-mL sample was filtered through a thin pad of Solka-Flock (washed with acetic acid), washed with acetic acid and evaporated to dryness on rotovap. The resulting oil was treated with a few mL of water to precipitate out the solid, and then put back onto rotovap to dry. The resulting white solid was analyzed by $^1$HNMR (CD$_3$OD) and HPLC. This whole procedure took about 30 min to complete. In $^1$HNMR (CD$_3$OD), the complete disappearance of the pyridine peaks at 7.32 and 8.40 ppm, indicate the complete consumption of starting material. HPLC (using the linear gradient condition described above) was used to monitor the amount of an impurity at RT= ~8.0 min, this impurity grows to significant amount when prolong hydrogenation took place. Starting material and product peaks came very close to each other, having the retention times of 6.76 and 6.80 respectively.

The reaction mixture was filtered through a pad of Solka-Flock (820 g, washed with 5 L acetic acid) and washed with acetic acid (14 L). The filtrate was concentrated to a thick oil containing approximately 1 kg acetic acid, in a batch concentrator fitted with 2 additional traps between the receiver and the house vac line at 60° C. (took about 5 h). DI water (15 L) was added to give a concentration of 1 g/15 mL 6% acetic acid in water and the resulting slurry was stirred for 18 h at room temperature. The solid was collected on a Buchner funnel lined with a sheet of shark-skin paper and a polypropylene pad (10 μm), washed with DI water (10 L) and dried under vacuum with nitrogen sweep to 1.03 kg (97%) of white solid.

If the amount of 5 is still higher than the specification, another swishing in 6% acetic acid in water (1 g/15 mL) (for at least 6 h) should be carried out. Typical recovery is around 92% with 3-fold reduction of 5.

HPLC Assay: 6 free base, 99.5 area %, RT=6.94 min; 5, RT=6.72 min; 1, RT=7.39 min; Zorbax RX-C8 column, 4.6 mm×25 cm ID; 220 nm; 1.5 mL/min; linear gradient 20 to 70% A over 12 min, A=CH$_3$CN, B=0.1% aqueous H$_3$PO$_4$.

mp 223°-225° C.

$^1$H NMR (CD$_3$OD) δ0.88 (t, J=7.3 Hz, 3H), 1.33 (m, 6H), 1.58 (m, 5H), 1.76 (m, 2H), 1.81 (m, 2H), 2.77 (t, J=7.5, 2H), 2.80 (m, 1H), 2.88 (m, 2H), 3.03 (B of ABX, J$_{BA}$=13.9 Hz, J$_{BX}$=4.6 Hz, 1H), 3.30 (m, 2H), 3.90–4.0 (m, 3H), 6.80 (d, J=8.5 Hz, 2H), 7.18 (d, J=8.5 Hz, 2H).

Anal. Calcd for C$_{22}$H$_{37}$O$_5$N$_2$S: C, 59.84; H, 8.40; N, 6.34; S, 7.24. Found: C, 59.98; H, 8.40; N, 6.40; S, 7.24.

Step 4b

To a 22 L 3-neck RB flask equipped with a mechanical stirrer, nitrogen inlet and an addition funnel was charged 6 free base (316.0 g, 0.717 mol) and isopropyl acetate (9.5 L). The mixture was stirred at room temperature (19° C.) for 10–15 min, then concentrated hydrochloric acid (120 mL) was added dropwise. The addition took about 40 min and the temperature remained at 19° C. throughout addition. The mixture was then stirred at room temperature (19° C.) for a further 5 hours. The product was isolated by filtration under nitrogen. The solid product was washed with isopropyl acetate (2×1 L) and suction-dried under nitrogen overnight to afford 6 HCl monohydrate (348 g) in 98% yield.

HPLC Assay: 6, 99.8 area %; RT=6.79 min; Zorbax RX-C8 column, 4.6 mm×25 cm ID; 220 nm; 1.5 mL/min; linear gradient 10 to 90% A over 10 min, A=CH$_3$CN, B=0.1% aqueous H$_3$PO$_4$; or L-700,462, 99.8 area %, RT=6.94 min; 5, RT=6.72 min; 1, RT=7.39 min; Zorbax RX-C8 column, 4.6 mm×25 cm ID; 220 nm; 1.5 mL/min; linear gradient 20 to 70% A over 12 min, A=CH$_3$CN, B=0.1% aqueous H$_3$PO$_4$.

Chiral HPLC: L-isomer, >99.9%; RT=10 min; D-isomer, <0.1%; RT=8.5 min; ULTRON-ES-OVM column, 4.6 mm×25 cm, 5 m, with guard column; 220 nm; 0.7 mL/min; isocratic, 90% Buffer (6 g ammonium formate adjusted to pH 4.1 with formic acid), 10% MeOH.

mp1 87°-88° C., mp2 131°-132° C.; [α]$^{25}$D=−14.4° (c 0.92, MeOH).

$^1$H NMR (CD$_3$OD) δ0.84 (t, J=7.3 Hz, 3H), 1.23 (hex, J=7.3 Hz, 2H), 1.30–1.70 (m, 9H), 1.75 (m, 2H), 1.95 (m, 2H), 2.64 (t, J=7.4 Hz, 2H), 2.77 (A of ABX, JAB=13.9 Hz, JAX=9.8 Hz, 1H), 2.95 (m, 2H), 3.11 (B of ABX, JBA=13.9 Hz, JBX=4.6 Hz, 1H), 3.47 (m, 2H), 3.95 (t, J=6.2 Hz, 2H), 4.09 (X of ABX, JXA=9.8 Hz, JXB=4.6 Hz, 1H), 6.84 (d, J=8.6 Hz, 2H), 7.18 (d, J=8.6 Hz, 2H).

$^{13}$C NMR (CD$_3$OD) δ14.0, 22.5, 24.0, 26.5, 30.0, 30.4, 34.8, 36.8, 39.0, 45.3, 54.1, 59.4, 68.7, 115.5, 130.4, 131.7, 159.6, 175.2.

IR (Nujol, cm$^{-1}$) 3520, 3208, 3166, 2800–2300, 1727, 1610, 1595, 1324, 1256, 1141, 1119, 829.

HRMS calcd for C$_{22}$H$_{37}$N$_2$O$_5$S 441.2423, found 441.2423 (MH$^+$—H$_2$O—Cl)

Anal. Calcd for C$_{22}$H$_{39}$O$_6$ClN$_2$S: C, 53.37; H, 7.94; N, 5.66; Cl, 7.16; S, 6.48. Found: C, 53.56; H, 8.04; N, 5.62; Cl, 7.36; S, 6.53.

What is claimed is:

1. A process for preparing compounds of the following formula:

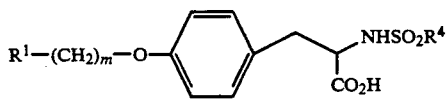

wherein:
R$^1$ is 4-piperidinyl or 4-pyridinyl;
m is an interger from two to six; and
R$^4$ is aryl, C$_{1-10}$ alkyl, or C$_{4-10}$ aralkyl,
according to the process steps whereby

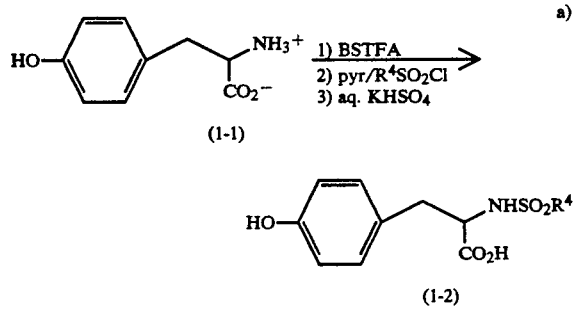

tyrosine or tyrosine-derivative (1-1) is subjected to bis(trimethylsilyl) trifluoroacetamide (BSTFA) mediated sulfonylation, using R$^4$SO$_2$Cl, to give the corresponding sulfonamide (1-2);

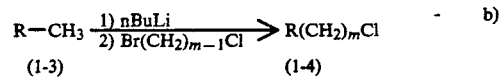

R is 4-pyridinyl, methylated 4-picoline (1-3) is reacted with n-BuLi, before quenching with a straight chain alkyl group having Br at one end and Cl at the other end, to yield

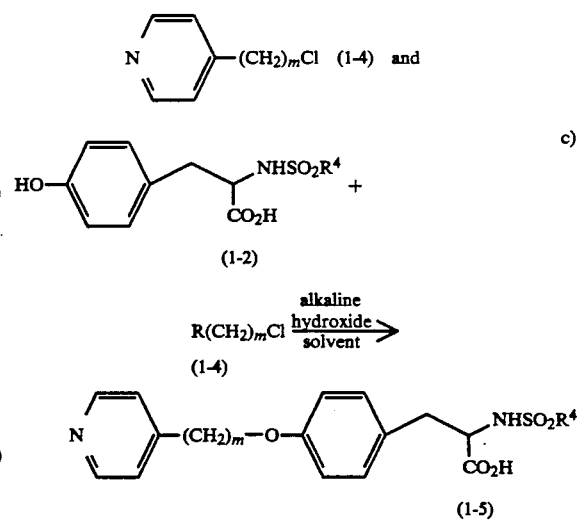

(1-2) is added to (1-4) and subjected to phenolic O-alkylation in aqueous alkaline hydroxide in a highly polar aprotic solvent; and when R$^1$ is optionally 4-piperidinyl, further selectively hydrogenating product (1-5) using Pd/C in acetic acid.

2. A process according to claim 1, wherein

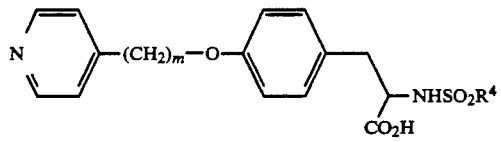 (1-5)

is selectively hydrogenated using Pd/C in acetic acid to form

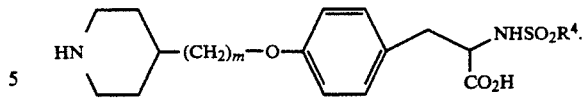

3. A process of claim 2 wherein sulfonylation step a) is conducted in acetonitrile.

4. A process of claim 2 wherein phenolic O-alkylaton step c) is conducted in a highly polar aprotic solvent selected from 1,3-dimethyl-3,4,5,6-tetra-hydro-2(1H)-pyrimidinone or methyl sulfoxide, in 3N KOH, at about 65° C.

* * * * *